United States Patent
Sugiura (10) Patent No.: US 10,098,977 B2
(45) Date of Patent: Oct. 16, 2018

(54) DEODORANT COMPOSITION AND DEODORIZING PRODUCT

(71) Applicant: TOAGOSEI CO., LTD., Minato-ku (JP)

(72) Inventor: Koji Sugiura, Nagoya (JP)

(73) Assignee: TOAGOSEI CO., LTD., Minato-ku (JP)

(*) Notice: Subject to any disclaimer, the term of this patent is extended or adjusted under 35 U.S.C. 154(b) by 11 days.

(21) Appl. No.: 15/516,605

(22) PCT Filed: Sep. 14, 2015

(86) PCT No.: PCT/JP2015/076061
§ 371 (c)(1),
(2) Date: Apr. 3, 2017

(87) PCT Pub. No.: WO2016/103808
PCT Pub. Date: Jun. 30, 2016

(65) Prior Publication Data
US 2018/0221528 A1    Aug. 9, 2018

(30) Foreign Application Priority Data

Dec. 26, 2014    (JP) .................................. 2014-266202

(51) Int. Cl.
| | |
|---|---|
| *A61L 9/01* | (2006.01) |
| *A61L 9/014* | (2006.01) |
| *B01J 20/16* | (2006.01) |
| *B01J 20/28* | (2006.01) |
| *B01J 20/06* | (2006.01) |
| *B01J 20/22* | (2006.01) |

(52) U.S. Cl.
CPC .............. *A61L 9/014* (2013.01); *B01J 20/06* (2013.01); *B01J 20/16* (2013.01); *B01J 20/22* (2013.01); *B01J 20/28016* (2013.01)

(58) Field of Classification Search
None
See application file for complete search history.

(56) References Cited

U.S. PATENT DOCUMENTS

2009/0272293 A1    11/2009    Ono
2010/0297053 A1    11/2010    Hirukawa

FOREIGN PATENT DOCUMENTS

| EP | 0 351 467 A1 | 1/1990 |
|---|---|---|
| JP | 63-246167 A | 10/1988 |
| JP | 7-813 A | 1/1995 |
| JP | 2000-279500 A | 10/2000 |
| JP | 2003-52800 | 2/2003 |
| JP | 2004-8357 A | 1/2004 |
| JP | 2006-256891 A | 9/2006 |
| JP | 2007-54328 A | 3/2007 |
| JP | 2008-210798 A | 9/2008 |
| JP | 2012-254925 A | 12/2012 |
| JP | 2013-22322 A | 2/2013 |
| JP | 2014-42728 A | 3/2014 |
| WO | 2004/058311 A1 | 7/2004 |
| WO | 2007/088879 A1 | 8/2007 |

OTHER PUBLICATIONS

International Search Report dated Dec. 1, 2015 in PCT/JP2015/076061 Filed Sep. 14, 2015.

*Primary Examiner* — Jessica Worsham
(74) *Attorney, Agent, or Firm* — Oblon, McClelland, Maier & Neustadt, L.L.P.

(57) ABSTRACT

The deodorant composition of the present invention includes an amorphous aluminum silicate, a hydrazide compound, and a crystalline zinc oxide in which at least two peaks among three peaks detected within a diffraction angle (2θ) range from 30 to 38 degrees when the crystalline zinc oxide is subjected to X-ray powder diffraction measurement have a half width of 0.4 to 1.2 degrees in an X-ray diffraction chart, wherein a content of the crystalline zinc oxide is in a range from 100 to 500 parts by mass based on 100 parts by mass of the hydrazide compound, and wherein a content of the amorphous aluminum silicate is in a range from 100 to 750 parts by mass based on 100 parts by mass of the hydrazide compound.

4 Claims, 2 Drawing Sheets

DEODORANT COMPOSITION AND DEODORIZING PRODUCT

TECHNICAL FIELD

The present invention relates to a deodorant composition that is suitable for at least two gases selected from an acidic gas, a basic gas, a sulfur-based gas, and an aldehyde gas, and to a deodorizing product that includes the deodorant composition.

BACKGROUND ART

In recent years, public interest in odor in daily life has grown, and stationary-type deodorizing products, spray-type deodorizing products, and various other deodorizing products (e.g., wallpaper, curtain, carpet, mat, sofa, filter, and clothes) that are provided with a deodorizing effect have been put on the market in order to deal with a demand for a reduction in an unpleasant odor or an offensive odor. Examples of the unpleasant odor or the offensive odor include a putrid odor (e.g., emitted from garbage), a human or animal excretion odor, sweaty odor, and aging odor, an aldehyde emitted from furniture and home appliances, a cigarette odor, and the like. Since an odor in daily life is normally a complex odor including a plurality of components, a combination of deodorizing components has been proposed so as to deodorize such a complex odor.

Activated carbon has been widely used as a deodorant. Since activated carbon is characterized by physical adsorption, it is difficult to use activated carbon as a general-purpose deodorant in various applications. Physical adsorption has a drawback in that a gas other than a gas that emits an offensive odor is continuously adsorbed in an open space irrespective of the type of gas component, and the adsorption capacity is immediately saturated. Moreover, when the adsorption capacity has been saturated, or the ambient temperature has increased, the adsorbed gas is released, and emits an offensive odor. Therefore, activated carbon can only be used for a product that can be replaced (exchanged). Since activated carbon has a black color, it is difficult to produce a white or chromatic deodorizing, product using activated carbon. In order to deal with the above problem, a deodorant that utilizes chemical adsorption and has a white or light color has been developed.

For example, Patent Document 1 discloses a deodorant that consists of a fine zinc oxide having a specific surface area of 40 to 100 $m^2/g$, a hydrogen sulfide deodorizing capacity of 3.0 mmol/g, and a primary particle size of 0.2 μm or less, and that is suitable deodorizing sulfur-based gas. Patent Document 2 discloses a deodorant that consists of particles in which zinc oxide and either or both of aluminum oxide and silicon oxide are closely bonded, and that is suitable for deodorizing an ammonia-based gas, an amine-based gas, or a sulfur-based gas. Patent Document 3 discloses a deodorant composition that includes a deodorant in which a compound having a primary amino group is supported on an organic or inorganic carrier (support), and a deodorant including aluminum silicate, and is suitable for deodorizing an aldehyde gas or a basic gas.

Patent Document 4 discloses an aluminum silicate having a BET specific surface area of 450 to 600 $m^2/g$ and a pore volume of 0.6 to 1.2 mL/g, and describes that this compound is a basic substance adsorbent. Patent Document 5 discloses a deodorant consisting of a layered zirconium phosphate represented by $Zr_{1-x}Hf_xH_x(PO_4)_6 \cdot nH_2O$.

Patent Document 6 discloses a deodorant that includes a metal complex of a hydrazide compound as an effective component, and is suitable for deodorizing an aldehyde gas or an acidic gas. Patent Document 7 discloses a deodorant for an aldehyde gas that includes a mixture including an aminoguanidine salt in which a pH becomes 1 to 7 when dissolved in purified water, and at least one compound selected from a silicate compound in which a pH becomes 2 to 8 when dispersed in purified water, a tetravalent metal phosphate compound in which a pH becomes 2 to 8 when dispersed in purified water, a zeolite in which a pH becomes 2 to 8 when dispersed in purified water, and a silica gel in which a pH becomes 2 to 8 when dispersed in purified water, wherein a pH of an aqueous suspension including the mixture becomes 1 to 7.

However, these chemical adsorption-type deodorants differ as to the reaction mechanism, and one deodorant can normally adsorb only one type of offensive odor. Therefore, it is necessary to use a plurality of deodorants in combination in order to deal with a complex odor.

For example, Patent Document 8 discloses a deodorant composition that includes an aldehyde gas deodorant in which at least one compound selected from the group consisting of succinic acid dihydrazide, carbohydrazide, and oxalic acid dihydrazide is supported on at least one compound selected from the group consisting of a silicate compound and a tetravalent metal phosphate, and at least one deodorant selected from the group consisting of a sulfur-based gas deodorant, a basic gas deodorant, and an organic acidic gas deodorant, and further a deodorant composition that includes an aldehyde gas deodorant in which at least one compound selected from the group consisting of saccinic acid dihydrazide, carbohydrazide, and oxalic acid dihydrazide is supported on a mixture including at least one compound selected from the group consisting of an aluminum silicate, a zeolite, and a tetravalent metal phosphate, and magnesium silicate, and at least one deodorant selected from the group consisting of a sulfur-based gas deodorant, a basic gas deodorant, and an organic acidic gas deodorant.

Patent Document 9 discloses an adsorbent composition that includes silicon dioxide, a water-insoluble phosphate of a tetravalent metal, and a hydroxide of a divalent metal, and is suitable for deodorizing an acidic gas and a basic gas.

Patent Document 10 discloses a deodorant for a film that includes a porous inorganic substance, an amine compound, and a metal oxide, and is suitable for deodorizing an aldehyde gas, a basic gas, and a sulfur-based gas, wherein the average particle size of at least one component is 5 to 30 μm.

Patent Document 11 discloses a deodorizing carpet having a nonwoven fabric onto which a deodorant that includes a porous inorganic substance, an amine compound, and a metal oxide is sprayed, and a skin layer consisting of pile yarns and a ground fabric.

PRIOR TECHNICAL DOCUMENT

Patent Document

[Patent Document 1] JP-A 2003-52800
[Patent Document 2] JP-A S63-246167
[Patent Document 3] JP-A 2000-279500
[Patent Document 4] JP-A 2006-256891
[Patent Document 5] JP-A 2012-254925
[Patent Document 6] JP-A 2007-54328
[Patent Document 7] WO 2007/088879
[Patent Document 8] WO 2004/058311

[Patent Document 9] JP-A H7-813
[Patent Document 10] JP-A 2013-22322
[Patent Document 11] JP-A 2014-42728

SUMMARY OF THE INVENTION

Problems that the Invention is to Solve

As described above, a deodorant having chemical adsorption normally deodorizes a specific offensive odor component. When a plurality of deodorants are used in combination in order to deodorize a complex odor, reactive groups included in the deodorants may interact and impair the deodorizing performance of each deodorant depending on the ratio and the like, whereby the overall deodorizing performance may deteriorate. In some case, a change in color or aggregation also occurs.

An object of the present invention is to provide a deodorant composition that exhibits an excellent deodorizing effect with respect to a complex odor including an acidic gas, a basic gas, a sulfur-based gas, an aldehyde gas, and the like, and exhibits excellent processability and versatility. Another object of the invention is to provide a deodorizing product that utilizes a deodorant composition.

Means for Solving the Problems

The present inventor found that a composition including a specific crystalline zinc oxide, an amorphous aluminum silicate, and a hydrazide compound has a very high deodorizing effect with respect to a complex odor including an acidic gas, a basic gas, a sulfur-based gas, an aldehyde gas, and the like. The inventor also found that a cloth and the like including the deodorant composition rarely shows a problem with respect to the outward appearance (e.g., change in color).

Specifically, one aspect of the present invention is a deodorant composition characterized in that the composition includes an amorphous aluminum silicate, hydrazide compound, and a crystalline zinc oxide in winch at least two peaks among three peaks detected within a diffraction angle (2θ) range from 30 to 38 degrees when the crystalline zinc oxide is subjected to X-ray powder diffraction measurement have a half width of 0.4 to 1.2 degrees in an X-ray diffraction chart, that a content of the crystalline zinc oxide is in a range from 100 to 500 parts by mass based on 100 parts by mass of the hydrazide compound, and that a content of the amorphous aluminum silicate is in a range from 100 to 750 parts by mass based on 100 parts by mass of the hydrazide compound. Another aspect of the present invention is a deodorizing product having the above deodorant composition.

Effects of the Invention

The deodorant composition of the present invention exhibits an excellent deodorizing effect with respect to a complex odor including an acidic gas, a basic gas, a sulfur-based gas, and an aldehyde gas through a chemical adsorption effect. It is necessary to adsorb 70% or more of acetic acid (30 ppm), ammonia (100 ppm), hydrogen sulfide (4 ppm), and acetaldehyde (14 ppm) in view of the odor strength of each gas and industrial standards. The deodorant-containing coating composition of the present invention has a performance comparable to or higher than the above performance.

The deodorant composition is in white or a light color, and can be used in a convenient manner. Since the deodorant composition exhibits excellent processability, a deodorizing product for various applications, a deodorant-containing coating composition that forms a deodorant coating or the like, a deodorant-containing resin composition that forms a resin molded article or a foamed article, and the like can be provided by utilizing the deodorant composition.

EMBODIMENTS FOR CARRYING OUT THE INVENTION

Hereinafter, the present invention is described in detail.

The deodorant composition of the present invention includes an amorphous aluminum silicate, a hydrazide compound, and a crystalline zinc oxide in which at least two peaks among three peaks detected within a diffraction angle (2θ) range from 30 to 38 degrees when the crystalline zinc oxide is subjected to X-ray powder diffraction measurement have a half width of 0.4 to 1.2 degrees in an X-ray diffraction chart in a specific ratio.

The deodorant composition of the present invention may include the crystalline zinc oxide, the amorphous aluminum silicate, and the hydrazide compound in the form of a powder, or a mixed powder of a crystalline zinc oxide, and a material in which a hydrazide compound is supported on an amorphous aluminum silicate powder.

Figure 1:
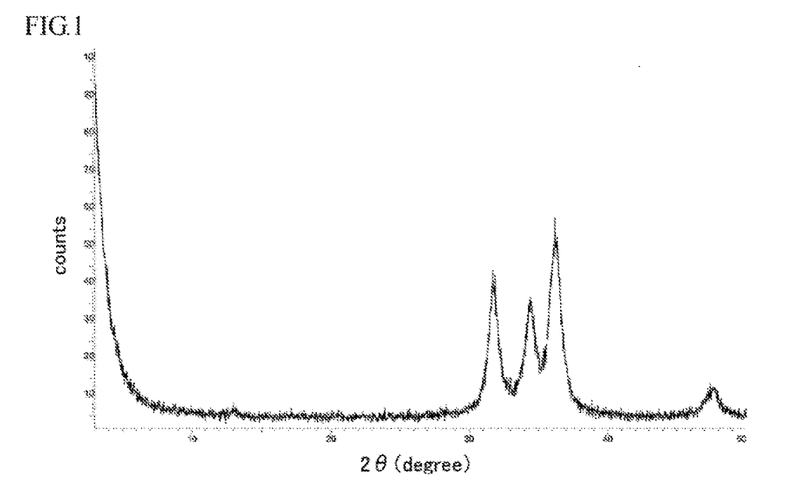
FIG. 1 illustrates an X-ray diffraction chart (wide range) of crystalline zinc oxide.
Figure 2:
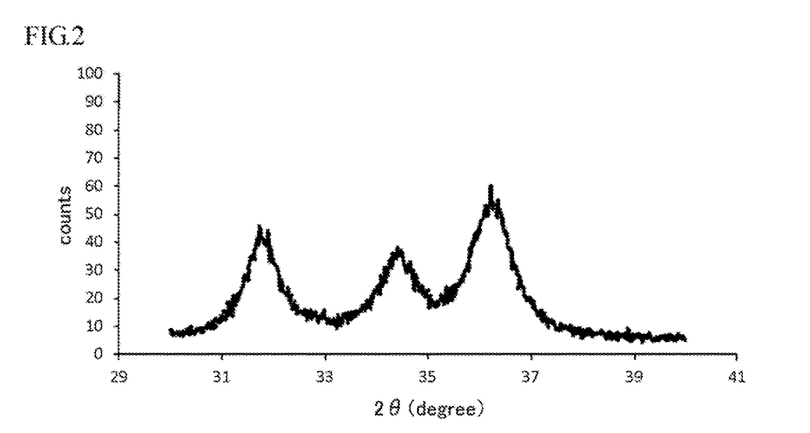
FIG. 2 illustrates an X-ray diffraction chart (narrow range) of crystalline zinc oxide.
Figure 3:
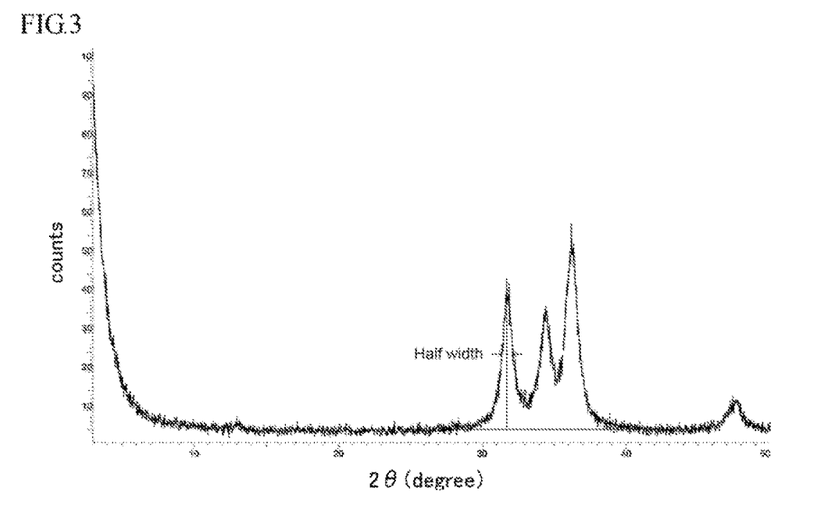
FIG. 3 is a schematic view illustrating a method that determines a half width of a peak detected in the X-ray diffraction chart of crystalline zinc oxide.

When the crystalline zinc oxide according to the invention is subjected to X-ray powder diffraction measurement, three peaks that are attributed to the crystal structure of zinc oxide are detected at diffraction angles (2θ) of about 31.7 degrees, about 34.4 degrees, and about 36.2 degrees (see FIGS. 1 and 2). A diffraction intensity of each peak differs depending on the measurement conditions. However, a half width of each diffraction peak is almost identical irrespective of the diffraction intensity. The half width can be determined as illustrated in FIG. 3. The half width of the crystalline zinc oxide is in a range from 0.4 to 1.2 degrees and preferably from 0.5 to 1.0 degrees from the viewpoint of the deodorizing performance with respect to a complex odor. Since a particle size of the crystalline zinc oxide is normally 100 nm or larger, the half width in the X-ray diffraction chart indicates crystallinity instead of the crystal grain size. The crystalline zinc oxide is characterized in that it is not a crystal that has excellent crystallinity, but has a specific crystallinity that differs from an amorphous state.

The crystalline zinc oxide may consist of zinc atom and oxygen atom. The crystalline zinc oxide may further include an additional atom such as aluminum atom, an alkali metal atom, an alkaline-earth metal atom and a transition metal atom as long as the crystalline zinc oxide has a half width within the above range.

The crystalline zinc oxide preferably a crystalline zinc oxide that includes aluminum atom and has crystallinity.

A particle diameter of the crystalline zinc oxide is not particularly limited. The crystalline zinc oxide is preferably in the form of a powder since a high deodorizing effect is obtained when the deodorant composition is used for a deodorant coating (including a deodorant point), a resin molded article, a foamed article, and the like, and a deodorant-containing coating composition or a deodorant-containing resin composition for producing these deodorant coating and the like exhibits excellent processability. In this case, a median particle size is preferably in a range from 0.1 to 5 μm, and more preferably from 0.5 to 3 μm. The maximum particle size of the crystalline zinc oxide is normally 20 μm or smaller, and preferably 15 μm or smaller.

A BET specific surface area of the crystalline zinc oxide is preferably 70 m²/g or more, more preferably in a range from 90 to 200 m²/g, and further preferably from 120 to 160 m²/g. The deodorant having the specific surface area of 70 m²/g or more exhibits a high deodorizing effect.

According to the Lab color space, the crystalline zinc (powder) has preferably an L value of 92 to 98, an a value of −1 to −6, and a b value of 4 to 10, and more preferably an L value of 94 to 97, an a value of −1.5 to 5, and a b value of 5 to 9.

A gas adsorption capacity of the crystalline zinc oxide is preferably 20 mL/g or more with respect to acetic acid gas, and 70 mL/g or more with respect to hydrogen sulfide gas. The term "adsorption capacity" used herein refers to the maximum amount of an odor component (i.e., acetic acid or hydrogen sulfide) that can be deodorized, absorbed, or adsorbed by the compound. The adsorption capacity is measured as described below. The deodorant is put in a test bag that is formed of a material (e.g., vinyl alcohol-based polymer or polyester) on which the odor component is rarely adsorbed and which does not allow air to pass through. After sealing the test bag, an odor gas is injected into the test bag. The odor gas concentration in the test bag is measured immediately after the odor gas has been injected, and after a given time has elapsed. A difference between the residual gas concentration after a given time has elapsed and the initial gas concentration is taken as the amount of odor gas that has been deodorized, absorbed, or adsorbed by the deodorant.

A production method of the crystalline zinc oxide is not particularly limited. An arbitrary raw material, production process, equipment, and the like may be used to produce the deodorant. An outline of a method for producing the crystalline zinc oxide is described below.

An aqueous slurry containing a zinc oxide particle in an amount of 1% to 20% by mass is prepared, and carbon dioxide gas is introduced into the aqueous slurry for several hours to produce a basic zinc carbonate particle. After that, water is removed from the resulting slurry containing the basic zinc carbonate particle to obtain a dry powder, which is heated at a temperature from about 100° C. to about 400° C. to obtain crystalline zinc oxide aggregates having the above configuration. The crystalline zinc oxide aggregates are pulverized to obtain a crystalline zinc oxide powder that is suitably used as the deodorant composition of the present invention.

As described above, the crystalline zinc oxide according to the invention may include an additional atom. A crystalline zinc oxide having an additional atom may be obtained by adding an aqueous dispersion or an aqueous solution including a compound that has the additional atom to the aqueous slurry including zinc oxide when implementing the above method for producing the crystalline zinc oxide.

The amorphous aluminum silicate according to the present invention may be either natural amorphous aluminum silicate or synthetic amorphous aluminum silicate. The amorphous aluminum silicate may include an additional atom such as an alkali metal atom, alkaline-earth metal atom and transition metal atom in addition to silicon atom, aluminum atom and oxygen atom.

For example, a synthetic amorphous aluminum silicate is represented by a following general formula.

$$Al_2O_3 \cdot nSiO_2 \cdot mH_2O$$

(In the formula, n is an integer equal to or larger than 6, and m is an integer.)

The synthetic amorphous aluminum silicate is more preferably an amorphous aluminum silicate in which n and m in the above general formula are respectively an integer from 6 to 50 and an integer from 1 to 20, and particularly an amorphous aluminum silicate in which n and m are respectively an integer from 8 to 15 and an integer from 3 to 15, from the viewpoint of the deodorizing effect with respect to ammonia gas and the like.

When the aluminum silicate is amorphous in the present invention, the odor component adsorption effect is improved and deterioration in adsorption performance when used in combination with an additional deodorant is reduced. The amorphous aluminum silicate has an indefinite shape, and only a broad peak is detected when the amorphous aluminum silicate is subjected to X-ray powder diffraction measurement.

A particle diameter of the amorphous aluminum silicate is not particularly limited. The amorphous aluminum silicate is preferably particulate since a high deodorizing effect is obtained when the deodorant composition is used for a deodorant coating (including a deodorant point), a resin molded article, a foamed article, and the like, and a deodorant-containing coating composition or a deodorant-containing resin composition for producing these deodorant coating and the like exhibits excellent processability. In this case, a median particle size is preferably in a range from 1 to 10 μm, more preferably from 1 to 5 μm, and further preferably from 1 to 3 μm. The maximum particle size of the amorphous aluminum silicate is normally 30 μm or smaller, and preferably 15 μm or smaller.

A BET specific surface area of the amorphous aluminum silicate is preferably in a range from 20 to 800 m²/g, and more preferably from 200 to 600 m²/g. If the specific surface area of the amorphous aluminum silicate is small, the odor gas adsorption performance may decrease.

An ammonia gas adsorption capacity of the amorphous aluminum silicate is preferably 30 mL/g or more, and more preferably 35 mL/g or more. The adsorption capacity is measured as described above.

A production method of the amorphous aluminum silicate is not particularly limited. For example, the amorphous aluminum silicate may be produced by reacting a water-soluble silicate and a water-soluble aluminum salt so that a ratio (Si/Al ratio) of silicon atoms included in the water-soluble silicate to aluminum atoms included in the water-soluble aluminum salt is preferably 2 to 8.3 to prepare a reaction mixture having a pH of 3.5 to 5.0, aging the reaction mixture at a temperature ranging from 60° C. to 120° C. for 5 minutes to 3 hours, and washing, drying and pulverizing a cake obtained by solid-liquid separation.

As described above, the amorphous aluminum silicate according to the invention may include an additional atom. An amorphous aluminum silicate having an additional atom may be obtained by adding an aqueous dispersion or an aqueous solution including a compound that has the additional atom when mixing the water-soluble silicate and the water-soluble aluminum salt when implementing the above method for producing the amorphous aluminum silicate.

The hydrazide compound according to the invention not particularly limited as long as the hydrazide compound is a compound having a hydrazide group (—NH—NH$_2$). At least one of a monohydrazide and a polyhydrazide may be used as the hydrazide compound. Examples of the monohydrazide include a compound represented by R$^1$CONHNH$_2$ (wherein R$^1$ is a substituted or unsubstituted hydrocarbon group). A dihydrazide, a trihydrazide, a tetrahydrazide, and the like may be used as the polyhydrazide. Among these, a dihydrazide is preferable. Examples of the dihydrazide include a compound represented by H$_2$NHN—X—NHNH$_2$ (wherein X is —CO— or —CO—Y—CO—, and Y is a substituted or unsubstituted divalent hydrocarbon group). In the present invention, a dihydrazide such as oxalic acid dihydrazide, malonic acid dihydrazide, succinic acid dihydrazide, adipic acid dihydrazide, sebacic acid dihydrazide, tartaric acid dihydrazide, malic acid dihydrazide, isophthalic acid dihydrazide, terephthalic acid dihydrazide, and carbohydrazide are preferably used.

These hydrazide compounds may be used singly in combination of two types thereof. Since a hydrazide compound may have a large particle size, it may be difficult to uniformly mix a hydrazide compound with an additional deodorant. Therefore, it is preferable to use the hydrazide compound in a state in which the hydrazide compound is supported on an additional deodorant such as an amorphous aluminum silicate powder.

The hydrazide compound may be caused to be supported on an amorphous aluminum silicate powder as described below. A solution including the hydrazide compound such as succinic acid dihydrazide and carbohydrazide is added dropwise to or sprayed onto an amorphous aluminum silicate powder while stirring. Subsequently, the mixture is dried at a temperature preferably from 60° C. to 120° C. and more preferably from 80° C. to 110° C. When the mixture is then heated at a temperature preferably from 140° C. to 220° C., and more preferably from 170° C. to 200° C., a hydrazide compound supported amorphous aluminum silicate powder having excellent water resistance can be obtained.

Content ratio of the crystalline zinc oxide, amorphous aluminum silicate and hydrazide compound in the deodorant composition of the present invention is not particularly limited. The content ratio that reliably provides advantageous effects of the present invention is as follows. A content of the crystalline zinc oxide is in a range from 100 to 500 parts by mass, preferably from 150 to 450 parts by mass, and further preferably from 200 to 400 parts by mass based on 100 parts by mass of the hydrazide compound content. A content of the amorphous aluminum silicate is in a range from 100 to 750 parts by mass, preferably from 150 to 750 parts by mass, and further preferably from 200 to 700 parts by mass based on 100 parts by mass of the hydrazide compound content.

A production method for the deodorant composition of the present invention is not particularly limited. The deodorant composition of the present invention may be produced by a method that dry-mixes the components, or may be produced by a method that wet-mixes the components. It is particularly preferable to dry-mix the components within a short time without heating the components.

The deodorant composition of the present invention preferably has an adsorption capacity of 20 mL/g or more with respect to acetic acid gas, 80 mL/g or more with respect to ammonia gas, 50 mL/g or more with respect to hydrogen sulfide gas, and 10 mL/g or more with respect to acetaldehyde gas. The above adsorption capacity is reliably obtained when the deodorant composition has a median particle size of 3 µm or less and a maximum particle size of 20 µm or less. If the median particle size is too large, the processability of the deodorant composition may deteriorate.

There has been a tendency that, when a plurality of deodorants is used in combination, the deodorizing performance of each deodorant is negated, and the total deodorizing performance is insufficient. On the other hand, the deodorant composition of the present invention shows only a small decrease in deodorizing performance. It is difficult to determine whether or not a decrease in deodorizing performance has occurred when a dry mixing method is used. Specifically, when the components are wet-mixed, a decrease in deodorizing performance may occur due to a reaction between the reactive groups. Since a combination that has such optimum balance is rare, it is considered that the combination of the components included in the deodorant composition of the present invention is such a rare optimum combination. When the deodorant composition of the present invention is brought into contact with water, the resulting liquid has an almost neutral pH. Therefore, the deodorant composition of the present invention rarely poses a problem, and exhibits excellent processability even when used for the applications described later.

The deodorant composition of the present invention has a deodorizing effect, and may be put in a container (e.g., cartridge) in the form of a powder or granules to produce a deodorizing product, for example. When the deodorizing product is placed in the vicinity of an indoor or outdoor offensive odor emission source, the concentration of a component that emits an unpleasant odor or an offensive odor can be reduced. The deodorant composition of the present invention may be used in combination with other materials to produce a deodorizing product used for various applications, a deodorant-containing coating composition that forms a deodorant coating or the like, a deodorant-containing resin composition that forms a resin molded article or a foamed article, and the like (as described in detail below).

One example of a useful deodorizing product that utilizes the deodorant composition of the present invention is a deodorizing fiber. Examples of the deodorizing fiber include a deodorizing fiber (1) in which the deodorant composition adheres to, or is bonded to, the surface of a raw material fiber, and a deodorizing fiber (2) in which the deodorant composition is embedded in a raw material fiber so as to be exposed from the surface of the raw material fiber. The raw material fiber may be a natural fiber or a synthetic fiber. The raw material fiber may be a short fiber, a long fiber, a composite fiber having a sheath-core structure, or the like. The deodorizing fiber (1) may be obtained by applying a deodorant-containing liquid composition such as an aqueous or organic solvent-based suspension that includes the deodorant composition to the surface of a raw material fiber using a coating method, a dipping method, or the like, and removing the medium (e.g., solvent). The deodorant-containing liquid composition may contain an adhesive that improves the adhesion of the deodorant composition to the surface of the raw material fiber. The pH of the aqueous suspension including the deodorant composition is not particularly limited, but is preferably adjusted to about 6 to 8 so that the deodorant composition exhibits sufficient performance.

The deodorizing fiber (2) may be obtained by adding the deodorant composition of the present invention to a molten liquid of a resin for forming fibers, or a resin solution of a resin for forming fibers in which the resin is dissolved, and forming a fiber using the resulting deodorant-containing resin composition. The resin for forming fibers used for this method is not particularly limited, but a resin constituting publicly known chemical fiber may be used. Examples of a preferable resin include a polyester resin, a polyamide resin, an acrylic resin, a polyethylene resin, a polyvinyl resin, a polyvinylidene resin, a polyurethane resin, a polystyrene resin, and the like. These resins may be a homopolymer or a copolymer. When the resin is a copolymer, the monomers may be polymerized in an arbitrary ratio.

A content of the deodorant composition in the deodorant-containing resin composition is not particularly limited. It is normally possible to obtain a higher deodorizing performance, and maintain the deodorizing performance for a long time by increasing the content of the deodorant composition. However, a significant difference in deodorizing effect may not occur even when the content of the deodorant is increased to a large extent, or the strength of the deodorizing fiber may be decreased when the content of the deodorant is increased to a large extent. Therefore, the content is preferably in a range from 0.1 to 20 parts by mass, and more preferably from 0.5 to 10 parts by mass based on 100 parts by mass of the resin for forming fibers.

The deodorizing fiber having the deodorant composition of the present invention may be used for a textile product such as cloths (e.g., underwear, sock, and apron), nursing clothes, bedclothes, a cushion, a blanket, a carpet, a sofa, an air filter, a quilt cover, a curtain, a car seat, and a product obtained by processing the deodorant sheet described later.

Another major application for the deodorant composition of the present invention is the deodorant-containing coating composition as mentioned above. An oil/fat or a resin used as the main component of a vehicle that is used in case of producing the deodorant-containing coating composition is not particularly limited. A natural vegetable oil, a natural resin, a semi-synthetic resin, or a synthetic resin may be used. Examples of the oil/fat and the resin include a drying oil and a semi-drying oil such as linseed oil, Chinese tung oil, and soybean oil, rosin, cellulose nitrate, ethyl cellulose, cellulose acetate butyrate, benzyl cellulose, a novolac-type or resol-type phenolic resin, an alkyd resin, an amino-alkyd resin, an acrylic resin, a vinyl chloride resin, a silicone resin, a fluororesin, an epoxy resin, a urethane resin, a saturated polyester resin, a melamine resin, a polyvinylidene chloride resin, and the like. The deodorant-containing coating composition may be a thermoplastic composition or a thermo-setting composition.

A content of the deodorant composition of the present invention in the deodorant-containing coating composition is not particularly limited. It is normally possible to obtain a higher deodorizing performance, and maintain the deodorizing performance for a long time by increasing the content of the deodorant. However, a significant difference in deodorizing effect may not occur even when the content of the deodorant is increased to a large extent, or the coating surface may lose its gloss, or cracks may be formed when the content of the deodorant is increased to a large extent. Therefore, the content of the deodorant composition is preferably in a range from 0.1% to 20% by mass, and more preferably from 0.5% to 10% by mass based on a total amount of the composition.

The deodorant composition of the present invention can be used for both birth a liquid coating material and a powdery coating material. The deodorant-containing coating composition may be designed to form a coating through an arbitrary mechanism. When it is desired to cure the resulting coating, the deodorant-containing coating composition may be an oxidatively polymerizable composition, a moisture polymerizable composition, a thermally curable composition, a catalytically curable composition, a UV-curable composition, a polyol-curable composition, or the like. An additive (e.g., pigment and dispersant) that may be added to the composition is not particularly limited as long as the additive does not undergo a chemical reaction with the deodorant composition of the present invention. The deodorant-containing coating composition can be easily prepared. Specifically, the deodorant-containing coating composition can be prepared by sufficiently dispersing and mixing the raw material components using an ordinary mixing device such as ball mill, roll mill, disperser and mixer.

The deodorant-containing coating composition containing the deodorant composition of the present invention may suitably be used for (applied to) an inner wall or outer wall of a building, a vehicle, a railroad vehicle, and the like; a garbage incineration plant; a garbage container; and the like.

A further application of the deodorant of the present invention is a deodorizing sheet (including a deodorizing film). A raw material sheet for the deodorizing sheet is not particularly limited. A material for forming the raw material sheet, the microscopic structure of the raw material sheet, and the like may be selected taking account of the application and the like. The raw material sheet is preferably formed of an organic material such as a resin and paper, an inorganic material, or a composite material of these. It is preferable that the raw material sheet allow air to pass through from one side to the other side. Specific examples of a preferable raw material sheet include Japanese paper, a synthetic paper, a nonwoven fabric, a resin film, and the like. It is particularly preferable that the raw material sheet be a paper formed of either or both of a natural pulp and a synthetic pulp. When a natural pulp is used, the deodorant particle easily enters the space between the fibers that are finely branched, and a practical carrier (support) can be obtained without using a binder. On the other hand, a synthetic pulp exhibits excellent chemical resistance. When the synthetic pulp is used, it may be difficult to support the deodorant particle (powder) between the fibers. In order to suppress the occurrence of such a situation, part of the fibers may be melted in a drying step that is performed after papermaking so that the adhesion between the powder and the fibers increases, or fibers formed of another thermosetting resin may be mixed. Paper for which various properties are adjusted can be obtained by utilizing natural pulp and synthetic pulp in an appropriate ratio. It is normally possible to obtain paper that exhibits excellent strength, water resistance, chemical resistance, oil resistance, and the like by increasing the ratio of synthetic pulp, and obtain paper that exhibits excellent water absorption, gas permeability, hydrophilicity, formability, texture, and the like by increasing the ratio of natural pulp.

The deodorizing sheet may have a structure in which the deodorant composition is included in the entire raw material sheet from one side to the other side, or may have a structure in which the deodorant composition is provided in a surface layer situated on one side or the other side of the raw material sheet, or may have a structure in which the deodorant composition is provided only inside the raw material sheet.

A supporting amount of the deodorant composition of the present invention included in the deodorizing sheet is not particularly limited. It is normally possible to obtain a higher deodorizing performance, and maintain the deodorizing performance for a long time by increasing the content of the deodorant composition. However, a significant difference in deodorizing effect may not occur even when the amount of deodorant composition supported on the deodorizing sheet is increased to a large extent. Therefore, the supporting amount of the deodorant composition is preferably in a range from 0.1 to 10 parts by mass based on 100 parts by mass of the raw material sheet.

A production method of the deodorizing sheet is not particularly limited. The deodorant composition of the present invention may be supported when producing the raw material sheet, or may be supported after producing the raw material sheet. For example, the deodorant composition may be supported in paper by applying a method that introduces the deodorant composition in an arbitrary step of the papermaking process, a method that applies the deodorant-containing liquid composition including an adhesive to paper that has been produced in advance using a coating method, an immersion method, or a spray method, or the like. It is preferable to apply the deodorant-containing liquid composition so that the deodorant composition is supported in an amount of about 0.05 to 10 $g/m^2$.

Hereinafter, a method that introduces the deodorant composition during a papermaking process is described as an example of a method for producing a deodorizing sheet in which the deodorant composition of the present invention is supported on paper. The papermaking process may be performed according to a publicly known method. First, a slurry including the deodorant composition and pulp in a specific ratio is prepared, and then a cationic flocculant and an anionic flocculant are added to the slurry respectively in a ratio of 5% or less by mass based on a total amount of the slurry to produce an aggregate (flock). Subsequently, the aggregate is subjected to the papermaking process according to a publicly known method. After that, the resulting paper is dried at a temperature from 100° C. to 190° C. to obtain a deodorizing sheet in which the deodorant composition is supported on paper.

The deodorizing sheet having the deodorant composition of the present invention may be used as a medical packing paper, a food packing paper, an electric device packing paper, a nursing paper product, a freshness-keeping paper, paper clothes, an air-cleaning filter, a wallpaper, a tissue, a toilet paper, and the like.

The deodorant composition of the present invention may be applied to a resin molded article or a foamed article, as described above. The resin molded article is produced using the deodorant-containing resin composition as a molding material. The deodorant-containing resin composition may be a mixture or a molten mixture that includes a thermoplastic resin and the deodorant composition. The resin molded article can be produced by charging the deodorant-containing resin composition into a molding machine. A pellet-like resin containing the deodorant composition at a high concentration may be prepared in advance, and mixed with the main resin, and the mixture may be charged into a molding machine. An additive such as a pigment, a dye, an antioxidant, a light stabilizer, an antistatic agent, a blowing agent, an impact modifier, glass fibers, a dampproof agent and an extender may optionally be added to the deodorant-containing resin composition in order to improve the properties of the deodorant-containing resin composition. The resin molded article or the foamed article may be produced by applying an ordinary molding method such as injection molding method, extrusion molding method, inflation molding method, vacuum forming method, and expansion molding method.

The resin molded article or the foamed article that includes the deodorant composition of the present invention may be used as (for) a home appliance (e.g., air cleaner and refrigerator), a common household product (e.g., trash box and drainer), a nursing product (e.g., portable toilet), and the like.

EXAMPLES

Hereinafter, the present invention is specifically described using Examples. The present invention is not limited to the Examples.

1. RAW Materials for Producing Deodorant Composition

Deodorants (d1) to (d11) for Examples and Comparative Examples are as follows properties of each deodorant are listed in Table 1.

1-1. Deodorant (d1)

Carbon dioxide gas was introduced into an aqueous slurry including zinc oxide in an amount of 10% by mass at a temperature of 40° C. for 6 hours while stirring the aqueous slurry. Subsequently, water was removed from the slurry. The dried product was heated at 300° C. to obtain a powder of crystalline zinc oxide. The diffraction peaks of the crystalline zinc oxide powder detected by XRD at diffraction angles of 31.7° and 36.2° both had a half width of 0.8 degrees. The crystalline zinc oxide powder was used as the deodorant (d1). The median particle size and the deodorizing capacity of the deodorant (d1) are listed in Table 1.

1-2. Deodorant (d2)

A powder of crystalline zinc oxide for pigment "Type II" (trade name) manufactured by Sakai Chemical Industry Co., Ltd. was used as the deodorant (d2). The diffraction peaks of the deodorant (d2) detected by XRD at diffraction angle of 31.7° and 36.2° both had a half width of 0.2 degrees (see Table 1).

1-3. Deodorant (d3)

A powder of crystalline zinc oxide "NANOFINE" (trade name) manufactured by Sakai Chemical Industry Co., Ltd. was used as the deodorant (d3). The diffraction peaks of the deodorant (d3) detected by XRD at diffraction angle of 31.7° and 36.2° both had a half width of 1.4 degrees (see Table 1).

1-4. Deodorant (d4)

A powder of hydrotalcite "DHT-A4" (trade name) manufactured by Kyowa Chemical Industry Co., Ltd. was used as the deodorant (d4). The median particle size and the deodorizing capacity of the deodorant (dl4) are listed in Table 1

1-5. Deodorant (d5)

A powder of synthesized amorphous magnesium aluminate was used as the deodorant (d5). The median particle size and the deodorizing capacity of the deodorant (d5) are listed in Table 1.

1-6. Deodorant (d6)

A powder of zirconium hydroxide (reagent) was used as the deodorant (dl6). The median particle size and the deodorizing capacity of the deodorant (d6) are listed in Table 1.

1-7. Deodorant 07)

A powder of synthesized layered titanium phosphate was used as the deodorant (d7). The median particle size and the deodorizing capacity of the deodorant (d7) are listed in Table 1.

1-8. Deodorant (d8)

A powder of synthesized amorphous aluminum silicate was used as the deodorant (d8). The median particle size and the deodorizing capacity of the deodorant (d8) are listed in Table 1.

1-9. Deodorant (d9)

A powder of synthesized crystalline aluminum silicate was used as the deodorant (d9). The medium particle size and the deodorizing capacity of the deodorant (d9) are listed in Table 1.

1-10. Deodorant (d10)

A powder of adipic acid dihydrazide manufactured by Otsuka Chemical Co., Ltd. was used as the deodorant (d10). The deodorizing capacity of the deodorant (d10) is listed in Table 1.

1-11. Deodorant (d11)

A powder of succinic acid dihydrazid manufactured by Japan Finechem Inc. was used as the deodorant (d11). The deodorizing capacity of the deodorant (d11) is listed in Table 1.

2. Production and Evaluation of Deodorant Composition and Deodorizing Product

Deodorant compositions (C1) to (C17) including the deodorant Table 1 in the ratio listed in Table 2 were produced. A deodorant-containing liquid composition including the resulting deodorant composition and an acryl-based binder dispersion was spread over a cloth formed of polyester fibers to obtain a deodorizing cloth. A deodorizing test was then performed using acetic acid, ammonia, hydrogen sulfide, or acetaldehyde. The results are listed in Table 2.

Examples 1 to 3 and Comparative Examples 1, 2, 5, 9, and 11 to 14

Since the deodorant (d10) and (d11) were water-soluble, these were each dissolved in water in advance. The aqueous

TABLE 1

| Deodorant | | Half width (degrees) | | Median particle | Deodorizing capacity (mL/g) | | |
|---|---|---|---|---|---|---|---|
| Type | Component | at 31.7° | at 36.2° | size (μm) | Acetic acid | Ammonia | Hydrogen sulfide |
| d1 | Crystalline zinc oxide | 0.8 | 0.8 | 1.0 | 33 | | 101 |
| d2 | Crystalline zinc oxide | 0.2 | 0.2 | 0.3 | 3 | | 20 |
| d3 | Crystalline zinc oxide | 1.4 | 1.4 | 2.0 | 12 | | 106 |
| d4 | Hydrotalcite | — | — | 0.5 | 50 | | |
| d5 | Amorphous magnesium aluminate | — | — | 2.0 | 37 | | |
| d6 | Hydrous zirconium oxide | — | — | 2.0 | 39 | | |
| d7 | Titanium phosphate | — | — | 0.5 | | 110 | |
| d8 | Amorphous aluminum silicate | — | — | 2.0 | | 43 | |
| d9 | Crystalline aluminum silicate | — | — | 1.0 | | 32 | |
| d10 | Adipic acid dihydrazide | — | — | — | | | |
| d11 | Succinic acid dihydrazide | — | — | — | | | |

Analyzing method and evaluating method for the deodorants (d1) to (d11) are as follows.

(1) Half Width of Diffraction Peak Detected By XRD

X-ray powder diffraction analysis (in which CuKα-rays were used) was performed using an X-ray diffractometer "RINT2400V" (type name) manufactured by Rigaku Corporation to obtain an X-ray diffraction chart. The tube voltage was set to 40 kV, and the current was set to 150 mA as measurement conditions. FIG 1 illustrates the X-ray diffraction chart of the deodorant (d1). In FIG. 1, three diffraction peaks between 30 and 38 degrees are attributed to zinc oxide. The half width of the peak at 31.7 degrees and the half width of the peak at 36.2 degrees were calculated. The peak width at 50% of the peak height was taken as the half width.

(2) Median Particle Size

The particle size d50 of the deodorant was analyzed (on a volume basis) using a laser diffraction particle size analyzer "MS2000" (type name) manufactured by Malvern. Note that the content in the particle size distribution is the volume ratio based on all of the particles. Since the density of the measurement target powder is constant, the content in the particle size distribution is the same as the value on a mass basis.

(3) Deodorizing Performance with Respect to Acetic Acid, Ammonia, or Hydrogen Sulfide 0.01 g of the dried deodorant powder was put in a test bag produced using a vinyl alcohol-based polymer film. After injecting 3 liters of acetic acid, ammonia, or hydrogen sulfide into the test bag, the test bag was allowed to stand for 1 hour. The residual gas concentration in the test bag was then measured using a gas detecting tube.

solution was then brought into contact with the deodorant (d8), and dried. A complex deodorant in which the deodorant (d10) or (d11) was supported on a surface of the deodorant (d8) was thus obtained. The resulting complex deodorant and the deodorant (d1) were dry-mixed to obtain deodorant compositions (C1) to (C5), (C8), (C12), and (C14) to (C17). Note that the deodorants were dry-mixed (stirred) at room temperature for 1 hour using a blender.

Comparative Examples 3, 6, and 10

The deodorants were mixed in the ratio listed in Table 2 to produce deodorant compositions (C6), (C9), and (C13).

Comparative Example 4

The deodorant (d10) was dissolved in water, and brought into contact with the deodorant (d1) in the same manner as those in Example 1 to obtain a complex deodorant in which the deodorant (d10) was supported on a surface of the deodorant (d1). The resulting complex deodorant was used as a deodorant composition (C7).

Comparative Examples 7 and 8

The deodorant (d10) was dissolved in water, and brought into contact with the deodorant (d1) in the same manner as those in Example 1 to obtain a complex deodorant in which the deodorant (d10) was supported on the surface of the deodorant (d1). The resulting complex deodorant and the deodorant (d9) or (d7) were dry-mixed to obtain deodorant compositions (C10) and (C11). Note that the deodorants were dry-mixed (stirred) at room temperature for 1 hour using a blender.

Deodorizing Test Using Deodorizing Cloth 2 parts by mass of the deodorant composition and 100 parts by mass of an acrylic binder dispersion having a solid content of 2% by mass were mixed to obtain a deodorant-containing liquid composition. The deodorant-containing liquid composition was applied to a cloth formed of polyester fibers so that the deodorant composition was spread in an amount of 1 g/m² to obtain a deodorizing cloth.

The deodorizing cloth was cut to obtain a test cloth having a size of 10×10 cm, and the test cloth was put in a test bag produced using a vinyl alcohol-based polymer film. After injecting 3 liters of a mixed gas of acetic acid (initial concentration 30 ppm), ammonia (initial concentration 100 ppm), hydrogen sulfide (initial concentration 4 ppm), and acetaldehyde (initial concentration 14 ppm) into the test bag, the test bag was allowed to stand for 2 hours. The residual gas concentration in the test bag was then measured using a gas detecting tube, and the reduction ratio was calculated. The above measurement was also performed using a polyester cloth to which the deodorant composition was not applied. The results are listed in Table 2.

TABLE 2

| | Deodorant composition | Deodorant (parts) | | | | | | | | | | | Reduction ratio (%) | | | |
|---|---|---|---|---|---|---|---|---|---|---|---|---|---|---|---|---|
| | | d1 | d2 | d3 | d4 | d5 | d6 | d7 | d8 | d9 | d10 | d11 | Acetic acid | Ammonia | Hydrogen sulfide | Acetaldehyde |
| Example 1 | C1 | 1 | | | | | | | 5 | | | 1 | 91 | >99 | 96 | 94 |
| Example 2 | C2 | 2 | | | | | | | 4 | | | 1 | 98 | >99 | >99 | 90 |
| Example 3 | C3 | 4 | | | | | | | 2 | | | 1 | >99 | 92 | >99 | 96 |
| Comparative Example 1 | C4 | 6 | | | | | | | 1 | | | 1 | >99 | 56 | >99 | 67 |
| Comparative Example 2 | C5 | 1 | | | | | | | 8 | | | 1 | 59 | >99 | 66 | 64 |
| Comparative Example 3 | C6 | 3 | | | | | | | 4 | | | | >99 | >99 | >99 | <10 |
| Comparative Example 4 | C7 | 3 | | | | | | | | | | 1 | 97 | 63 | >99 | 50 |
| Comparative Example 5 | C8 | | | | | | | | 4 | | | 1 | 35 | >99 | <10 | >99 |
| Comparative Example 6 | C9 | 1 | | | | | | | | | | | >99 | 62 | >99 | <10 |
| Comparative Example 7 | C10 | 3 | | | | | | | | 4 | | 1 | 87 | 70 | 87 | 58 |
| Comparative Example 8 | C11 | 3 | | | | | | 4 | | | | 1 | 72 | 34 | 88 | 23 |
| Comparative Example 9 | C12 | | 3 | | | | | | 4 | | | 1 | 32 | >99 | 43 | >99 |
| Comparative Example 10 | C13 | | 3 | | | | | | | 4 | | | 28 | 81 | 32 | <10 |
| Comparative Example 11 | C14 | | | 3 | | | | | 4 | | | 1 | 78 | 61 | 90 | 68 |
| Comparative Example 12 | C15 | | | | 3 | | | | 4 | | | 1 | >99 | 41 | 44 | 87 |
| Comparative Example 13 | C16 | | | | | 3 | | | 4 | | | 1 | 85 | 66 | 34 | 79 |
| Comparative Example 14 | C17 | | | | | | 3 | | 4 | | | 1 | >99 | 88 | 54 | 90 |
| Base cloth | | | | | | | | | | | | | 30 | 35 | <10 | <10 |

From the results in Table 2, the reduction ratio (deodorizing ratio) with respect to acetic acid, ammonia, hydrogen sulfide, and acetaldehyde was more than 90% in Examples 1 to 3, being excellent, however, the reduction ratio (deodorizing ratio) with respect to acetic acid, ammonia, hydrogen sulfide, or acetaldehyde was 70% or less in Comparative Examples 1 to 14. It was thus confirmed that the deodorant composition of the present invention and the deodorizing product that includes the deodorant composition of the present invention have an excellent deodorizing effect.

INDUSTRIAL APPLICABILITY

The deodorant composition the present invention exhibits an excellent deodorizing effect with respect to a complex odor including an acidic gas, a basic gas, a sulfur-based gas, and an aldehyde gas. Since the deodorant composition of the present invention has a white or light color, it is possible to produce a white or chromatic deodorizing product using the deodorant composition of the present invention taking account of the object of the deodorizing product. The deodorant composition of the present invention also exhibits excellent processability when used for various deodorizing products. For example, when the deodorant composition of the present invention is in a form of fine particles, the deodorant composition can be easily applied to paper, fibers, and the like by means of application (coating), kneading, and the like, to provide deodorizing products in the form of paper, a nonwoven fabric, fibers, and the like that exhibit excellent deodorizing performance.

The invention claimed is:

1. A deodorant composition, comprising:
   an amorphous aluminum silicate;
   a hydrazide compound; and
   a crystalline zinc oxide in which at least two peaks among three peaks detected within a diffraction angle (2θ) range from 30 to 38 degrees when the crystalline zinc oxide is subjected to an X-ray powder diffraction measurement have a half width of 0.4 to 1.2 degrees in an X-ray diffraction chart;
   wherein a content of the crystalline zinc oxide is in a range of from 100 to 500 parts by mass based on 100 parts by mass of the hydrazide compound, and
   wherein a content of the amorphous aluminum silicate is in a range of from 100 to 750 parts by mass based on 100 parts by mass of the hydrazide compound.

2. The deodorant composition according to claim 1, wherein the crystalline zinc oxide and the amorphous aluminum silicate have a median particle size of 3 μm or smaller.

3. The deodorant composition according to claim 1 wherein the hydrazide compound is a dihydrazide represented by formula (I), $$H_2NHN—X—NHNH_2 \quad (I)$$

where X is —CO— or —CO—Y—CO—, and Y is a substituted or unsubstituted divalent hydrocarbon group.

4. A deodorizing product, comprising:
   the deodorant composition according to claim 1.

* * * * *